(12) United States Patent
Plaskon

(10) Patent No.: US 7,316,715 B2
(45) Date of Patent: Jan. 8, 2008

(54) POLYAXIAL SCREW FOR ACETABULAR CUP

(75) Inventor: Gregory E. Plaskon, Clifton, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 11/062,013

(22) Filed: Feb. 18, 2005

(65) Prior Publication Data

US 2006/0190090 A1    Aug. 24, 2006

(51) Int. Cl.
*A61F 2/32* (2006.01)
(52) U.S. Cl. .............................. 623/22.36; 623/22.22; 623/22.35
(58) Field of Classification Search ... 623/22.21–22.39
See application file for complete search history.

(56) References Cited

U.S. PATENT DOCUMENTS

| | | | |
|---|---|---|---|
| 5,531,554 A | | 7/1996 | Jeanson et al. |
| 5,607,426 A | | 3/1997 | Ralph et al. |
| 5,725,588 A | * | 3/1998 | Errico et al. ............. 623/22.36 |
| 5,888,204 A | | 3/1999 | Ralph et al. |
| 5,954,722 A | | 9/1999 | Bono |
| 6,228,121 B1 | * | 5/2001 | Khalili .................... 623/22.36 |
| 6,235,003 B1 | | 5/2001 | Dysarz |
| 6,575,975 B2 | * | 6/2003 | Brace et al. .................. 606/69 |
| 6,676,704 B1 | * | 1/2004 | Pope et al. ............. 623/18.11 |
| 6,692,529 B2 | * | 2/2004 | Shah ....................... 623/22.13 |
| 2001/0037112 A1 | | 11/2001 | Brace et al. |
| 2003/0060890 A1 | * | 3/2003 | Tarabishy ............... 623/22.12 |

FOREIGN PATENT DOCUMENTS

| | | |
|---|---|---|
| FR | 2739151 | 9/1995 |
| FR | 2790198 | 2/1999 |
| WO | WO-2004/028334 | 4/2004 |

\* cited by examiner

*Primary Examiner*—Anhtuan T. Nguyen
*Assistant Examiner*—David A. Izquierdo
(74) *Attorney, Agent, or Firm*—Lerner, David, Littenberg, Krumholz & Mentlik, LLP

(57) ABSTRACT

The invention relates to a device which is used for solidly connecting an acetabular cup shell to bone using at least one screw. According to the invention, the screw passes through a hole housing a ring mounted in the shell of the acetabular cup. The ring is mounted within an aperture of the shell and can be rotated therein about the longitudinal axis of the screw. The ring is a split-ring comprising a non-circular outer profile which co-operates with the non-circular profile of the hole which is disposed in the shell. In this way, when the ring is rotated in the hole and wedged in place therein, it is constricted thereby locking the screw to the shell in the desired position. Alternately the screw can have an enlarged thread adjacent it's head end to expand an internally threaded split-ring.

9 Claims, 9 Drawing Sheets

POLYAXIAL SCREW FOR ACETABULAR CUP

BACKGROUND OF THE INVENTION

The present invention relates to a device for solidly connecting a shell of a prosthetic acetabular cup to the acetabular bone mass. The device has at least one attachment element taking the form of a threaded rod or screw passing through at least one aperture or hole in the acetabular cup shell. The aperture in the shell includes a ring mounted therein such that it can lock the angular position of the screw in the shell after it is screwed into the bone. The shell can be in the form of a typical spherical acetabular cup shell for contacting the natural acetabulum.

Known screw-and-plate osteosynthesis systems must allow immobilizing one or more bone fragments in reference to others. It is known to use spherical head screws cooperating with a spherically-shaped aperture in a plate and bringing the plate into compression over the bone until the friction of the plate on the bone stabilizes the assembly. These assemblies allow choice of the angle of implantation of screws during the operation and cause a return movement and a compression of a detached bone fragment. Certain of these systems allow, due to the oblong shape of the aperture, made in the plate, compression of one bone fragment on another.

Use is also known of a second generation of screw-and-plate systems called monoaxial-locking and polyaxial-locking systems in which the strength of the assembly no longer depends on compression of the plate on the bone but on a fixation of the screw in the plate. These systems allow achieving assembly away from the bone with, for the more elaborate ones, the possibility of choosing the angle of implantation of screws during the operation while achieving strength sufficient for postoperative stresses.

One example of monoaxial-locking device is described in French patent publication FR-A-2,739,151. This device comprises a plate traversed by tapped tapered holes in which are wedged the tapered threaded heads of the screws after tightening. U.S. application Ser. No. 10/999,132 teaches a method of locking the polyaxial screw, the teachings of U.S. application Ser. No. 10/999,132 are incorporated herein by reference.

In existing monoaxial mechanisms, bone anchoring is sometimes improved by the introduction of screws with the axes between them not being parallel. To achieve such orientation of the screws, the plate to be fixed to the support can be provided with holes with axis non-orthogonal to the surface of the plate such that the orientation of the screw is provided by the orientation of the hole in the plate. The surgeon then has no freedom concerning the orientation of the screw to be fixed. This predetermined orientation may sometimes prove to be incompatible with anatomical constraints.

One example of a polyaxial locking mechanism is specifically described in French patent publication FR-A-2,790,198. This device comprises a plate equipped with a ring expanding radially during the threading of the screw to allow immobilization of the ring and then of the screw inside the hole of the plate. The expansion of the ring is obtained by a tapered threading of the screw and of the internal bore of the ring. Another polyaxial system is shown in U.S. Pat. No. 5,954,722.

A system is likewise known through patent DE 100 39 767 comprising a ring with spherical external shape being able to be adjusted inside a plate comprising a spherically-shaped aperture. The ring is transversed by a screw, whose head is housed in a bore of the ring. No locking system is described for the screw.

U.S. Pat. Nos. 6,235,003 and 6,575,975 relate to a system comprising a ring whose outside shape is spherical, orientable inside a plate comprising a spherical housing. The ring is transvered by a screw, whose head is housed in a cylindrical bore of the ring. Locking is obtained by expansion of the head of the screw using an additional tapered screw.

U.S. Pat. No. 5,531,554 relates to a system comprising a malleable-collar screw. The collar is restricted when it is driven into a tapered hole on the plate until it spreads beyond the said hole, since it expands due to elasticity to prevent the screw from being removed. Return movement of the collar of the screw to its initial shape also inhibits axial displacement of the screw in the sense of an extraction of the screw from the bore in the plate.

WO 2004/028334 A2 shows a non-circular ring mounted in a non-circular hole.

It should be noted that other systems achieve locking by introduction under force of the threaded head of the screw in the aperture of the plate. The force necessary for the deformation of the material in the aperture is significant. Moreover, risks from detachment of metal particles cannot be ruled out.

Finally Patent Publication US-A1-2001/037112 relates to a system comprising a ring whose outside shape is spherical, orientable inside a plate comprising a spherical aperture. The ring is transversed by a screw, whose head is housed in a cylindrical bore of the ring. Locking is obtained by expansion of the head of the screw using an additional tapered screw.

SUMMARY OF THE INVENTION

One aspect of the present invention relates to a device for solidly connecting a screw to an acetabular cup shell in which the design allows optimally bringing together the shell and screw in a pre-operative orientation of the screw. The device allows easy installation and removal of the assembly while offering good resistance to pull out and to the stresses exerted tangentially to the surface of the shell around the aperture or bore therethrough.

This aspect is achieved by a device for solidly connecting at least one screw to an acetabular cup shell which screw is implanted in a bone. The shell may have a plurality of bores, each for receiving a bone screw. At least one bore in the shell has a split-ring whose non-circular external profile cooperates with a non-circular internal profile of the bore in the shell.

Consequently, after insertion of the screw, the screw head may be clamped by rotationally driving the ring in the bore which collapses the ring. Thus at the same time as the ring is immobilized by wedging of the ring in the bore, the constriction of the ring causes the immobilization of the screw.

This device allows easy installation of the screw which is not, before the constriction of the ring, in contact with the ring. Moreover, bringing together of the shell and bone is done simply by screwing the bone screw, the distance between the shell and the bone being able to be adjusted as needed. Finally, locking is done using a simple tool that ensures the rotational turning of the ring to clamp on to the screw head.

The invention has as a further aspect a method for solidly connecting an acetabular cup shell to a bone screw embedded in bone. The shell having a hole housing a split-ring for engaging a head of the screw. The method consists of introducing the screw into a passageway in the ring which is disposed in the aperture on the shell. Screwing the screw to its final position then rotationally driving the ring to ensure, by constriction of the ring, the immobilization of the screw in the hole at the correct angle.

For this purpose, one embodiment of the invention has as one aspect a device for solidly connecting a shell of an acetabular cup to bone using at least one screw in the form of a threaded shank passing through a hole or aperture housing a ring. The ring is a split-ring whose non-circular external profile cooperates with the non-circular internal profile of the hole or aperture in the shell causing, upon rotation of the ring in the hole, a simultaneous immobilization by wedging of the ring in the hole, and a constriction of the split-ring ensuring the immobilization of the threaded screw such as by clamping around the head of the screw. In other words the rotation of the non-circular split-ring in the non-circular shell hole causes the inner diameter of the split-ring to be reduced around the screw head.

One such device allows easy installation of the screw that is not, before constriction of the ring, in contact with the ring. Moreover, bringing together the shell and the bone or underlying support is done simply by screwing, the distance between the shell and bone being able to be adjusted as needed. Finally, locking is done using a simple tool that ensures rotational driving the ring in the shell aperture.

The invention has a further aspect a method of installation of a device for solidly connecting an outer shell of an acetabular cup to a natural acetabulum, using at least one fixing element in the form of a threaded rod or screw. The screw passes through a hole or aperture in the shell, the hole housing a ring for clamping the head of the screw part, to be screwed into bone. The method consists of introducing the threaded rod or screw into the ring which is already disposed in the hole in the shell, then to drive the threaded screw to its final position and then rotationally driving or turning the ring to ensure by constriction of the ring around the threaded rod or screw to immobilize the threaded rod in the hole.

An alternate embodiment is provided wherein the split-ring is circular in shape, and includes a part-spherical surface about the central axis thereof and includes a threaded bore. The threaded bore engages a portion of the screw adjacent its head which expands the split-ring. Preferably this is accomplished by providing both the threaded bore and the screw head with increasing root diameters which engage to force the split-ring open when the head portion of the screw enters the ring. It would also be possible to use non-threaded conically tapered surfaces which engage to expand the split-ring when the head end of the screw enters the bore.

These and other aspects of the invention are achieved by a system for rigidly connecting a bone screw to an acetabular cup shell wherein the cup shell has at least one aperture therein formed by part-spherical radially inwardly facing surface extending from an internal surface of the shell to an external bone contacting surface of the shell. A split-ring having a part-spherical outer surface and an internal bore, which includes a slot in the wall of the split-ring, extending between the internal bore and the outer surface for receiving a bone screw. The bone screw has a head portion mountable within the internal bore of the split-ring. A non-circular outer surface of the ring may be rotated with respect to a non-circular aperture in the shell so that the engagement between the non-circular portions of the split-ring and shell cause the ring to simultaneously grip the head portion of the screw and wedge in the aperture of the shell thereby locking the three pieces in position. Alternately, the slot in the split-ring may be expanded by the engagement of tapered surfaces, such as tapered threaded surfaces, in both the split-ring bore and head portion of the screw.

BRIEF DESCRIPTION OF THE DRAWINGS

The invention will be well understood by reading the following description of embodiments, in reference to the included drawings in which.

DETAILED DESCRIPTION OF THE DRAWINGS

Figure 1:
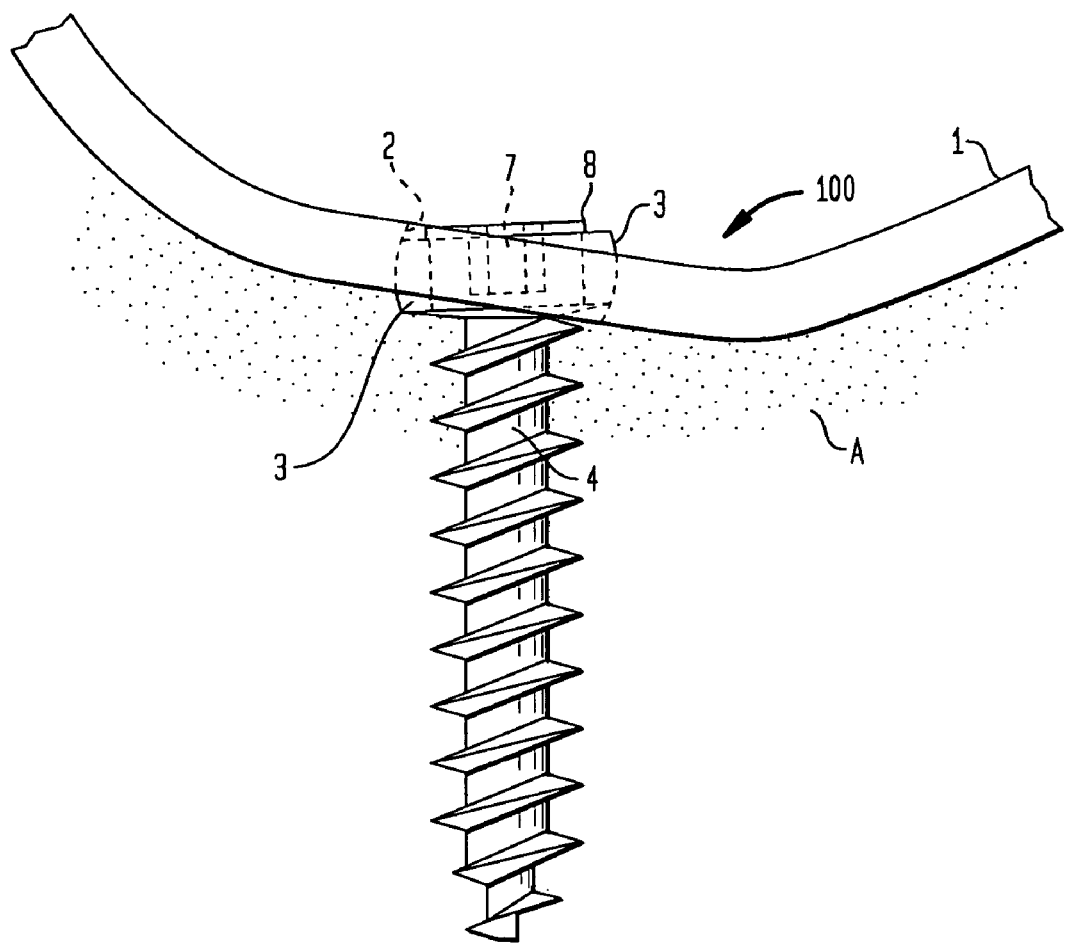
FIG. 1 is a front view partially in section of the connection device of the present invention in the assembled state.
Figure 2:
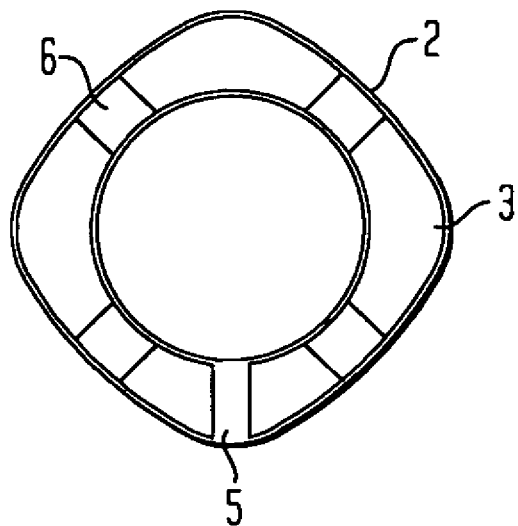
FIG. 2 is a top view of the non-circular ring in its non-circular hole in the absence of any constriction of the ring on the screw.
Figure 3:
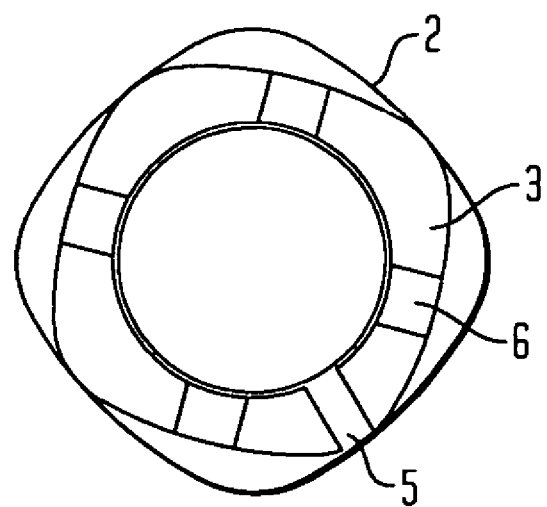
FIG. 3 is a top view of the ring in its hole in position of constriction of the ring on the screw.
Figure 4:
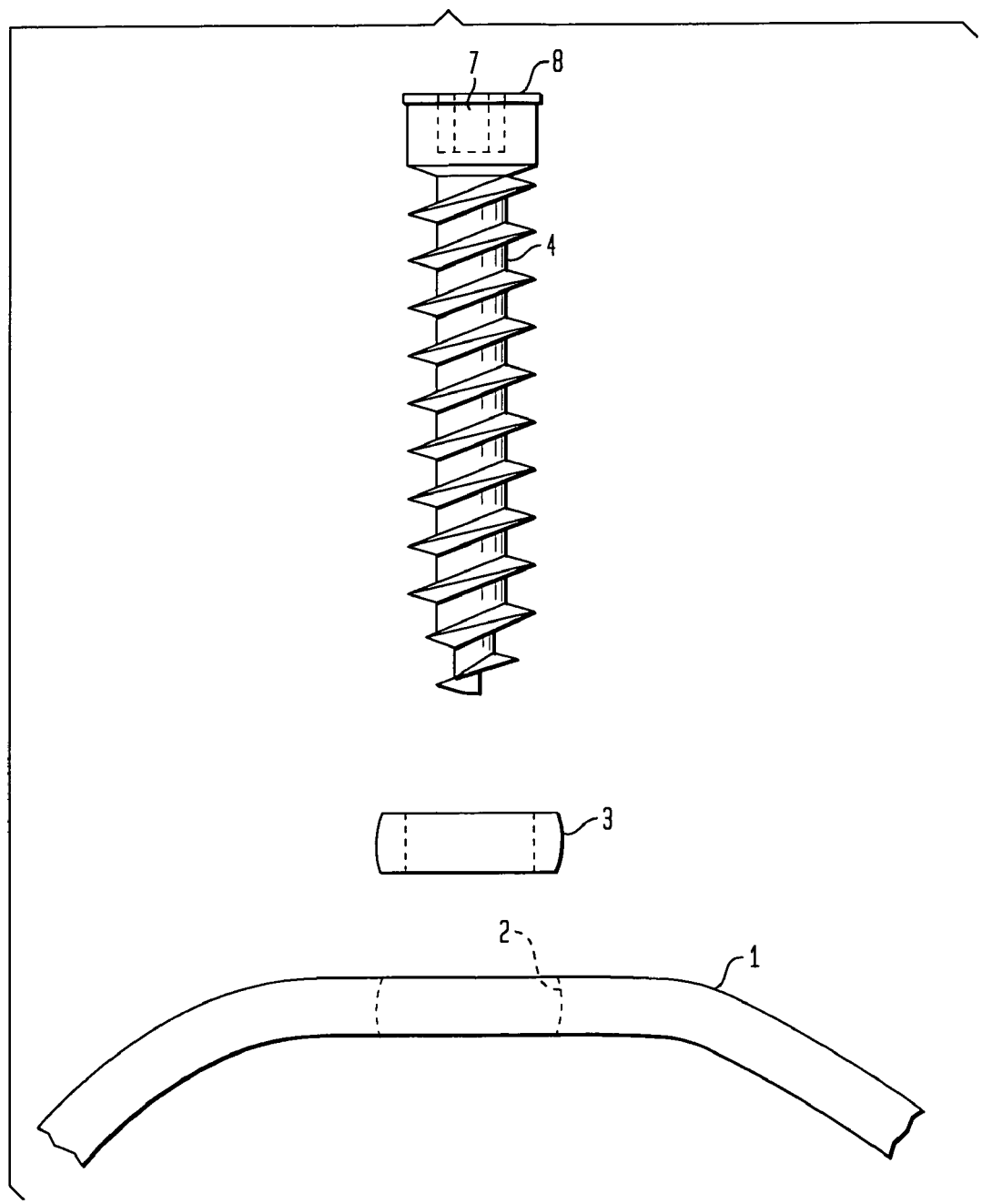
FIG. 4 is a front view partially in section of the device of FIG. 1 with the constituent elements unassembled.

Referring to FIGS. 1-5 there is shown a first embodiment of the connection device of the present invention generally denoted as 100, comprising a generally hemispherical shell 1 able to be solidly connected to the acetabulum A using a screw 4. Screw 4 comprises a threaded rod or a screw having a shank 4a threaded over at least part of its length. Rod or screw 4, ensures the solid connection of the shell to the bone A, passes through a non-circular hole or aperture 2 in the shell 1 and is anchored in the bone. Hole or aperture 2 is part-spherical in cross-section on moving from the outer bone contacting surface of the shell towards the inner surface of the shell. Preferably the hole 2 has an equator located at the midpoint of the shell thickness. The hole 2 of shell 1 is provided with a non-circular split-ring 3 having a bore transversed by screw 4. In the present invention, ring 3 can be partially collapsed at the time it is rotationally driven into the hole 2. This constriction of the inner diameter of ring 3 ensuring, generally by engagement with the head or end part of the thread of the screw 4, thus immobilizing the screw 4. At the same time, the ring 3 is immobilized by wedging ring 3 in the hole 2. This immobilization by wedging is achieved by friction of the external surface of the ring 3 against the internal surface of the hole 2. In effect, the non-circular external profile of the ring 3 cooperates with the non-circular internal profile of the hole 2 in the shell 1, so that at the same time as the constriction of the ring around the screw head there is a wedging of the ring 3 in the hole 2. It should be noted that the term circular must be understood in its strictest sense, that is to say where all points are equidistant from a fixed point. An example of possible embodiment of one such profile is specifically given in FIGS. 2 and 3. Profiles closer to circular profile may also be envisioned as shown in FIGS. 6 thru 8.

Figure 7:
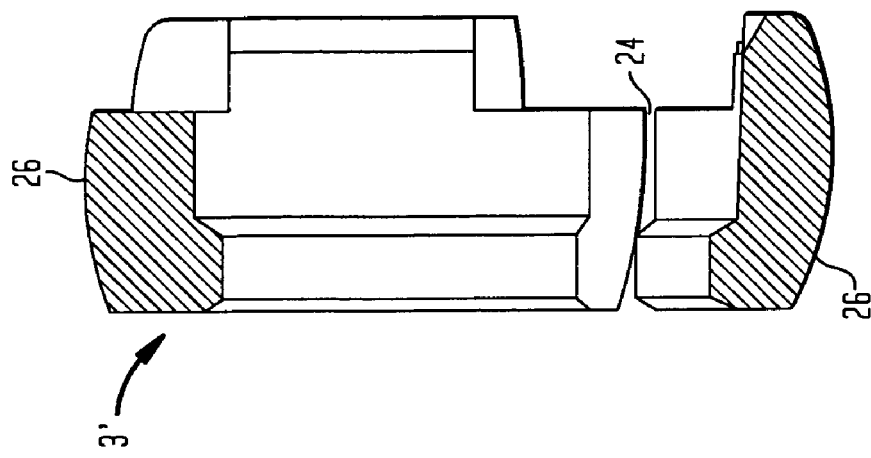
FIG. 7 is a cross-sectional view of the alternate split-ring shown in FIG. 6.
Figure 6:
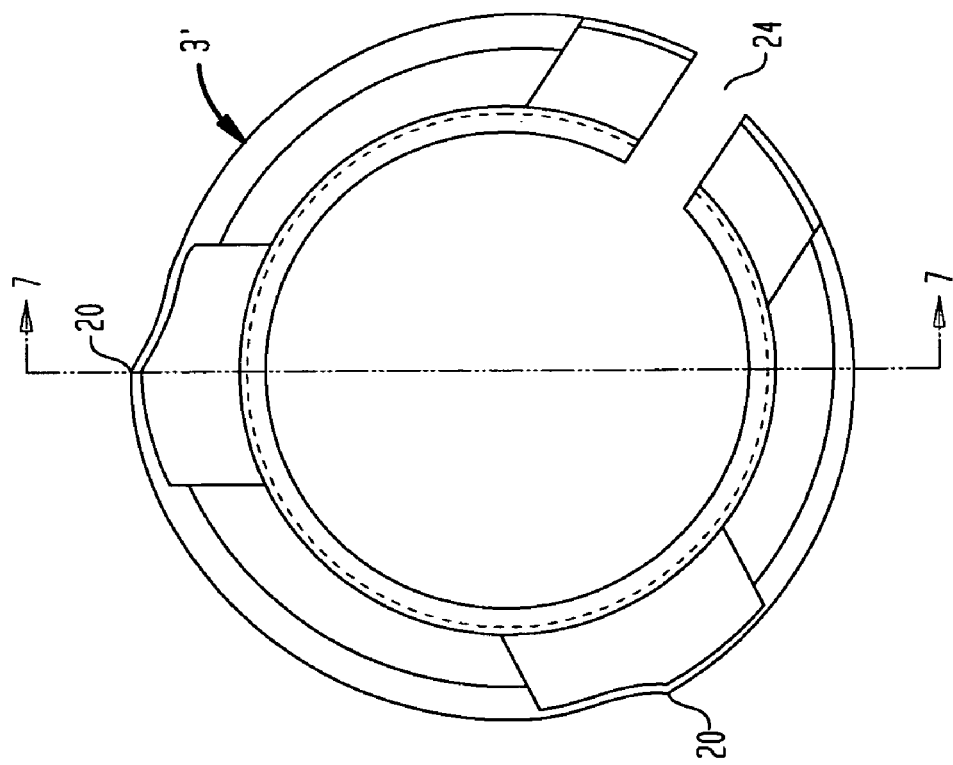
FIG. 6 is a top view of an alternate embodiment of the constriction split-ring of the present invention.
Figure 8:
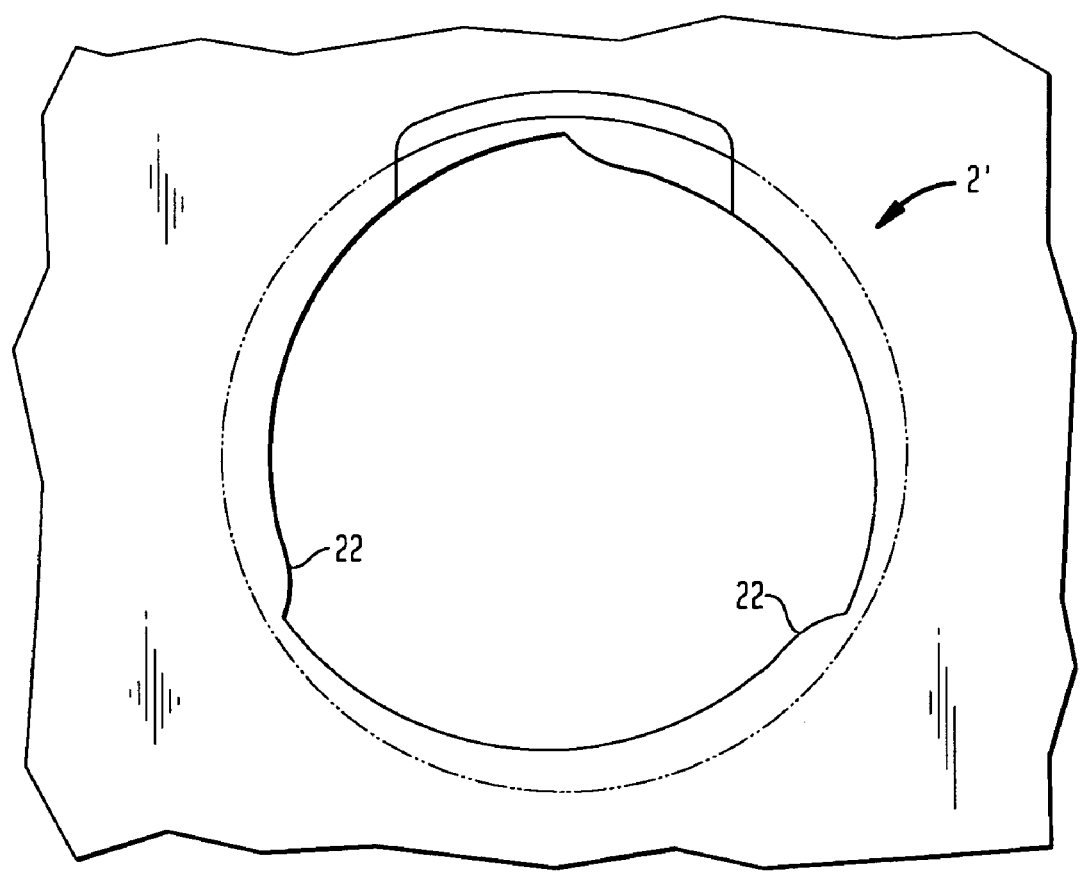
FIG. 8 is a top view of an aperture or hole in the plate showing a complimentary non-circular cross-section for use with the rings of FIGS. 6 and 7.
Figure 9:
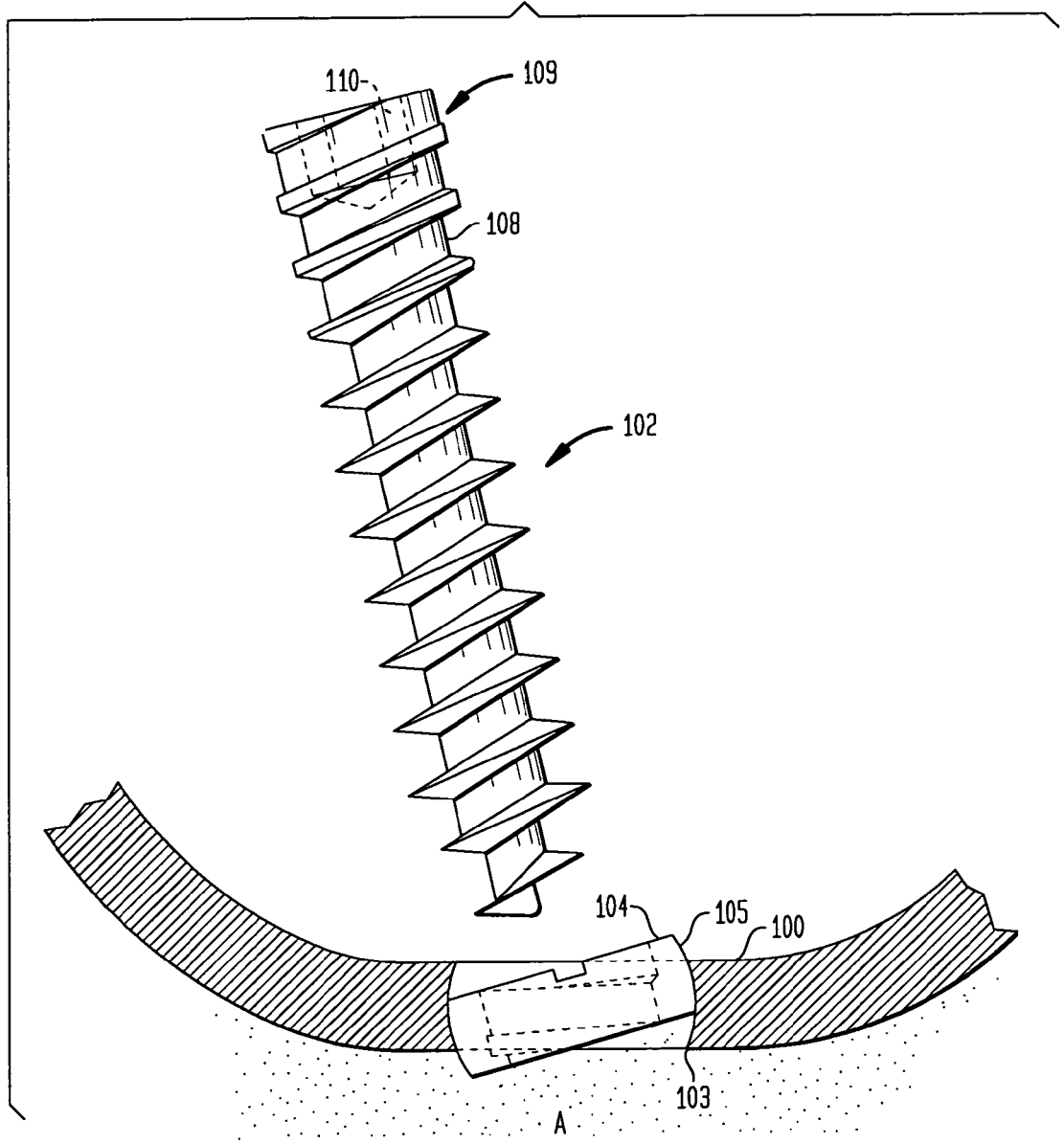
FIG. 9 is a front view, partially in section, of a second embodiment of the connection device of the present invention prior to assembly.
Figure 10:
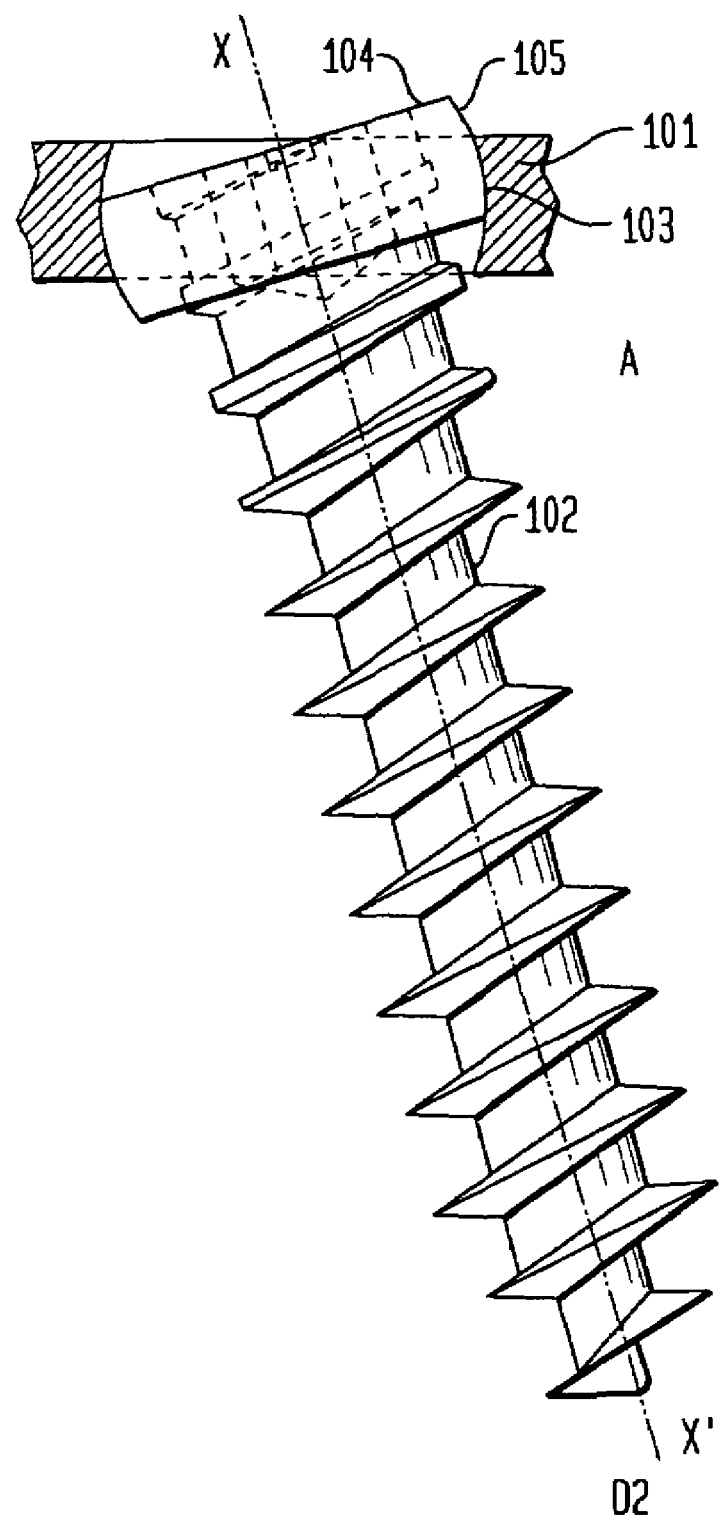
FIG. 10 is a front view, partially in section, of the connection device of the second embodiment shown in FIG. 9 in the assembled state.
Figure 11:
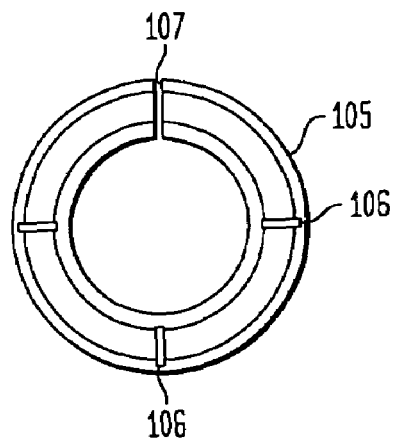
FIG. 11 is a top view of the ring of the second embodiment of the present invention.
Figure 12:
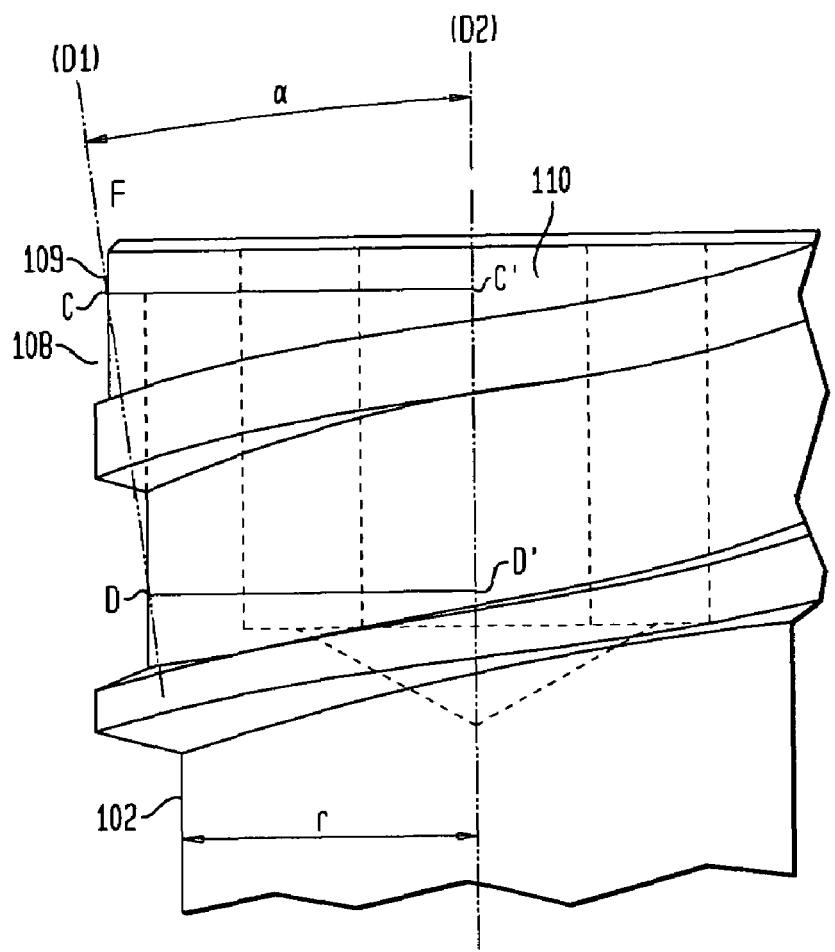
FIG. 12 is a front view of the head portion of the present invention showing the expanding root diameter of the head portion which engages a tapered or expanding root diameter of the bore in the ring of FIG. 11.

These alternate non-circular rings 3' shown in FIGS. 6 thru 8 are part-circular. The ring of FIG. 6 and the complimentary aperture of hole in an acetabular cup metal shell 1 is shown in FIG. 8 disclose an alternate non-circular design. Unlike the design of FIGS. 2 and 3 which have generally polygonal cross-sections the designs of FIGS. 6 thru 8 have radially offset portions 20 which interact with radially offset portions 22 of the aperture of FIG. 8 to cause contraction of slot 24. In this embodiment the radial offsets extend around 120 degrees of the entire circumference of the outer surface of the split-ring or the inner surface of the plate aperture. As in the preferred embodiment, split-ring 3' may have arcuate outer surfaces 26 to engage within internal part-spherical surfaces of the aperture in the shell. Also, a profile comprising two successive spiral parts may be used for the external profile of the ring and internal profile of the hole 2. These profiles may or may not be identical in shape. To facilitate constriction or circular narrowing of the ring 3' around the head of screw 4, ring 3' is slotted. The slot is more specifically shown as 5 in FIGS. 2 and 3. Constriction may also be achieved by deformation of deformable zones inside the body of the ring. Placing a slot however constitutes the simplest solution to achieve constriction, that is to say circular narrowing of the ring around the head or an upper threaded shank portion of the screw 4. Constriction takes place preferably by narrowing of slot 5 of ring 3, 3' around the head or the end portion of threaded rod or screw 4 that is generally unthreaded. This smooth head may have any shape. In the alternate design shown in FIGS. 9-12 it may also be possible to provide locking by expanding slot 5 assuming the screw head area expands in diameter on moving into the ring (103).

Two methods for using the embodiments of the invention may be envisioned.

In a first method of the invention according to FIG. 1, the ring 3 is moveably mounted inside generally spherical shaped hole 2 in shell 1. Furthermore, ring 3 takes the shape of a ring having a generally spherical outer surface divided by a slot and is housed inside a bore or aperture 2 which, as discussed above, is generally spherical in cross-section. The ring 3 has a shape complementary to the hole 2 of the part 1. The sphericity allows any axial orientation of the screw inside the hole to be achieved. Thus, the ring constitutes the equivalent of a pivot element within hole 2 about the longitudinal axis of screw 4.

The front face of preferred ring 3, 3' is provided with raised or projecting elements, such as the flutes 6, fitted to cooperate with a rotational drive tool for the ring 3. Rings 3, 3' may be premounted in the hole 2 of the part 1, such premounting preferably being done at the factory and is moveable in the hole 2 of the part 1. The threaded rod 4 comprises, at its drive end for screwing, at least one cavity 7, recessed or raised, intended to cooperate with a screw-driving tool. In the preferred example shown, screw 4 is provided, at its drive end, with a prismatic axial cavity suitable to receive the head of a rotational drive tool for screw 4 such as a hexagon socket.

The head of this threaded rod or screw is provided, at or in the vicinity of its drive end, with a shoulder 8 which may rest after the screw is fully inserted on the front face of the ring 3 located adjacent the cup inner surface to allow mating of the shell 1 with acetabulum A. This shoulder is more specifically shown in FIG. 1. One of the advantages of this device is to be able to vary as needed the distance between shell 1 and bone A even though the locking ring of the screw 4 is guaranteed regardless of the nature or of the quality of the interface between shell 1 and bone A (outer shell surface and bone surface).

Figure 5:
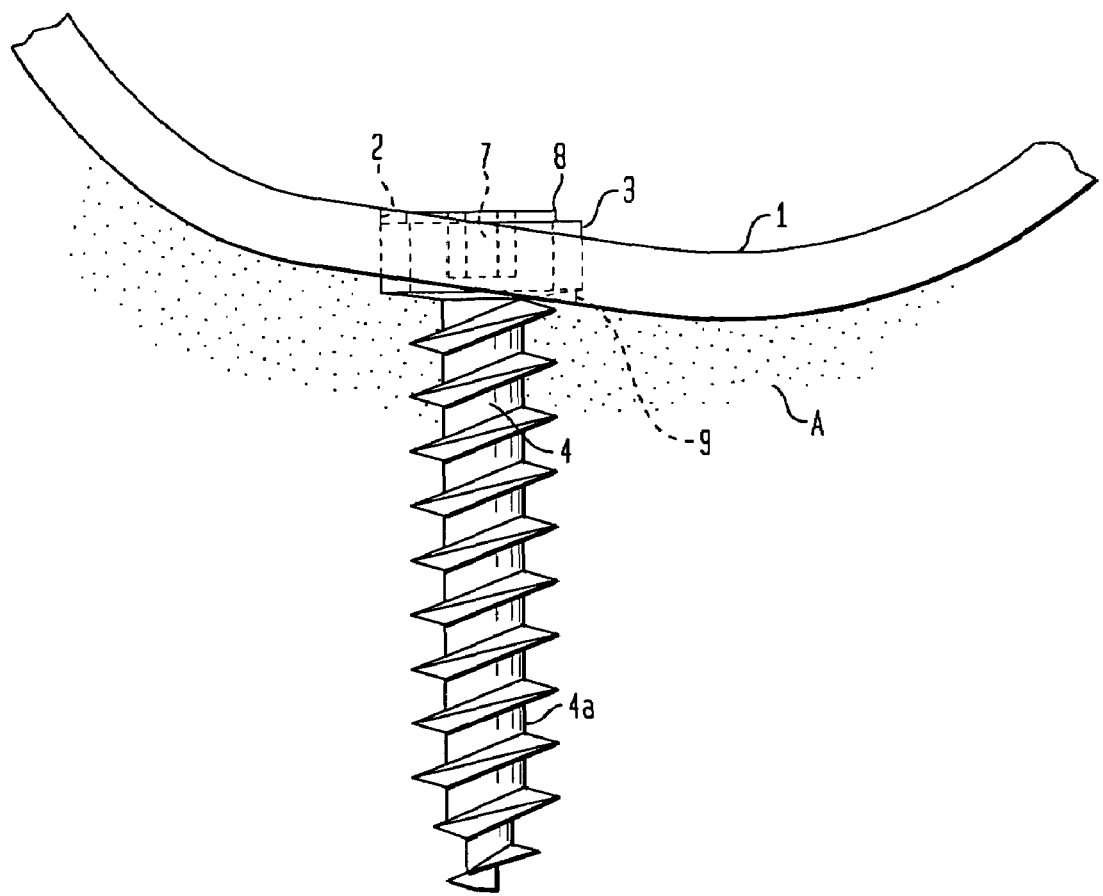
FIG. 5 is a front view partially in section of a second embodiment of a device according to the invention in unassembled state of the constituent elements.

In another embodiment of the invention shown in FIG. 5, the shell 1 is provided with a pre-oriented (angled) hole provided with an internal shoulder 9 for retaining the ring 3 inside the hole. This shoulder, housed in the bottom of the bore of the shell 1, retains the ring 3, 3' during the compression phase of the shell on the bone.

The method of installation of one such device is the following. It consists of introducing the screw 4 into the ring 3, the latter already disposed in the hole 2 of the shell 1. After threaded screw 4 is driven to its final position then ring 3, 3' is rotationally driven to ensure, by constriction of the ring 3, 3', immobilization of the screw in the hole 2. Thus the engagement of the high points of ring 3, 3' engage the sides of aperture 2 and deforms inwardly to lock the screw.

In a more detailed fashion, the phases of the installation of screw 4 are generally the following. The surgeon at first carries out a forming of the acetabular with a spherical reamer. The shell is then positioned on the bone. A drill guide is introduced into the ring housed inside the shell to allow orientation of the ring based on the orientation that surgeon wishes the screw 4 to have. The surgeon then proceeds with a drill using the drilling guide which allows positioning the axis of the threaded screw in the axis of the ring in such a way that the axis of the rod or screw and axis of the ring are absolutely coincident. The drilled depth is measured using a gauge. The screw is installed by rotational driving using a screwdriver. This screwing takes place until the mating of the shell on the bone. Shell 1 preferably has a plurality of holes each with a ring 3 for receiving a bone screw and the group of screws is installed. Once the group of screws is positioned, all the screws can then be locked to the plate 1 by tightening ring 3, 3' which is tightened by rotationally driving each ring using a fitted tool such as a spanner wrench. A self-tapping screw can be utilized which eliminates the drilling step.

In the use of one connecting device for solidly connecting the plate to the screw, no unscrewing, backward movement, or swiveling of the screw in its hole is noted. The screw is thus immobilized in all directions of movement, namely the direction of backward movement, the rotation of the screw around its own longitudinal axis, and the axis of rotational immobilization around the center of the sphere i.e. in polyaxial movement. The radial force that is applied at the time of rotational driving of the ring between external wall of the ring and the inside wall of the hole 2, is preferably exerted at at least three points. There would be the four sites of the ring 3 of FIGS. 2 and 3 or the three raised radial portions of FIGS. 6 thru 8. Constriction is generally achieved by narrowing of the slot 5.

In a second embodiment the devices shown in FIGS. 9-12 comprises a shell 101 suitable for implantation in an acetabulum A by means of at least one screw 102. The screw 102 itself comprises a threaded shank. Screw 102 which ensures the holding of shell 101 on bone A, goes through an orifice 103 of shell 101 and anchors to bone. Orifice 103 of shell 101 houses a split-ring 105 which is provided with an internally threaded bore 104 of increasing radius in direction of the internal face of shell 100. This tapered internally threaded bore 104 is intended to engage with a shank portion 108 of screw 102 during engagement by screwing screw 2 into orifice 103 of shell 100. The screw thread of the shank near the drive portion is outwardly tapered on moving toward the drive end of the screw (see FIG. 12). Shank 108 and internally threaded bore 104 of ring 105 are arranged in such a way as to ensure rotational immobilization by clamping of screw 102 in shell 101. This rotational immobilization is obtained by friction of the surfaces of ring 105 and bore 103. Split-ring 105 is similar to split-ring 3 in that it has a part-spherical shape to match the part-spherical cross-section of the aperture 103. Effectively, screw 102 presents, along a length D at least equal to one thread, a shank having a root diameter of radius r increasing in direction of the head end of the screw represented by 109 in the figures. This screw portion works together, at the time of its engagement in ring 105, with the internally threaded bore 104. This internally threaded bore 104 is likewise of radius increasing in direction of the internal face of shell 101 opposite the face in question of the bone A to obtain the desired clamping effect. Preferably the major diameter of the screw threads remain constant.

This clamping effect cannot be obtained unless the radius of the root diameter increases in appropriate manner. Effectively, as FIG. 13 shows, radius r of the shank 108 of screw 102 must increase in such a way that line D1, passing through two points, C, D chosen on the surface of the shank 8, in such a way that their orthogonal projection on the longitudinal axis D2 of the screw shank delimits a line segment D'C' in length equal to the screw pitch, forms with the longitudinal axis of the screw an angle a between 3 and 15 degrees. The shape of the shank of screw 102 matters little from the point where this progression of radius is compiled with. Furthermore, by way of example, the shank of screw 102 can assume, over a length at least equal to one thread, the shape of a surface of revolution developed by the rotation of a generatrix parallel to, and around, axis of revolution D2 consisting of the longitudinal centerline of screw 2 as it moves away. In this case, radius r of the root diameter of shank 108 of the screw successively assumes increasing values. The root of screw 2 of increasing radius may likewise assume a tapered shape not represented.

Generally, the portion of screw 2 with a root diameter of increasing radius r presents a profile homothetic to the profile of the internally threaded bore 104 of ring 105. Moreover, to obtain the desired effect of clamping by friction, the largest radius of the portion of bore 104 engaged with screw 102 is at most equal to the largest radius of the root diameter of screw 102. During use of this device in an acetabular cup shell, most of the time it is necessary that the head end 109 of screw 102 be arranged flush with the internal face of shell 101. In this case, the portion of screw 102 having a root diameter of increasing radius r is recessed at the head end 109 of screw 102 or in its proximity. For additional information relating to the manufacture of such a screw with constant pitch or not, one can refer in particular to patent application FR-A-2.739.151.

In a way characteristic of the invention, ring 105 is orientatably housed inside hole 103 of shell 101. Ring 105 is arranged to expand radially during the radial compression force exerted, by screw 102 during insertion to cause immobilization of screw permitting any angular orientation inside aperture 103 of shell 101. In this immobilized position, axis D2 (longitudinal centerline) of screw 102 and axis XX' (longitudinal centerline) of ring 105 are absolutely coincident.

To allow ring 105 to orient inside of orifice 103 in a pivoting manner, the external profile of ring 105 and the internal profile of aperture 103 of shell 101 are preferably complementary in shape. In the example shown in FIG. 9 and FIG. 10, ring 105 takes the shape of a split spherical ring, the slot being represented as 107 in FIG. 11. Further, for the securing of shell 101 to the bone, the surgeon proceeds as follows. He starts through the ring 105 with the drilling of an internal thread in the bony material, the centerline of this internal thread being chosen to obtain an orientation of the screw such that it withstands significant extraction forces. The threaded screw 102 is then inserted into the inside of ring 105 and comes in contact with internally threaded bore 104 thereof then is inserted into the centerline of the internal thread of the bore. During screwing of the threaded screw 102, at or on the proximity of, its head end for driving 109, comes to exert a radial compression force on the ring 105 and ensures the automatic expansion of the ring by the action of the screw. Screw 102 will then be immobilized and locked in a given position of orientation. Screwing continues until the radial expansion force is sufficient to exercise locking of the assembly (screw, ring and shell).

It should be noted that, to allow optimal coming together of shell 100 and ring 105, the face of ring 105 is provided with elements that protrude or are raised like grooves 106 matched to work with a drive tool in rotation of rod 2. These grooves 106 allow simultaneous rotational drive of screw 102 and ring 105. Effectively, screw 102 is generally provided at its head end 109 with a prismatic axial cavity 110 suitable for receiving the head of a rotational drive tool for screw 102. Ring 105 can be movably mounted inside aperture 103 of shell 101. In this case, an alignment marker slot can be provided to guarantee proper insertion of ring 105 in the orifice 103. The tool (not shown) can collapse split-ring 105 during insertion into the bone in the shell.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The ivention claimed is:

1. A system for rigidly connecting a bone screw to an acetabular cup shell, the system comprising:
   a part-spherical acetabular cup shell having an inner surface and an external bone-facing surface for contacting the natural acetabulum with at least one aperture therethrough said aperture having a non-circular profile side wall formed by a part-spherical radially inwardly facing surface extending from an inner surface of the shell to the external bone-facing surface of the shell;
   a split-ring having a non-circular external profile mounted in said aperture having a part-spherical outer surface for engaging said aperture side walls and a cylindrical internal bore and including a slot in a wall of said split-ring extending between said internal bore and said part-spherical outer surface of said split-ring;
   a bone screw having a head portion with a completely cylindrical outer surface mounted within the internal bore of the split-ring; and means for moving said wall of said split-ring with respect to said slot therein in a manner to simultaneously engage both the head portion of the bone screw and the side wall of the aperture in the shell by the rotational engagement of the non-circular profiles of the aperture and the split-ring.

2. The system as set forth in claim 1, wherein the split-ring has a central axis and is mounted inside the aperture of the shell in a manner wherein the central axis of the ring is moveable within the aperture.

3. The system as set forth in claim 1, wherein the split-ring takes the form of a slotted ring being housed inside said generally part-spherical surface in said aperture, said surface complementary to the outer surface of said ring.

4. The system as set forth in claim 1, wherein the split-ring is mounted in the aperture of the shell prior to insertion of the screw.

5. The system as set forth in claim 1 wherein said bone screw head portion slidably engages the internal bore of the split-ring.

6. The system as set forth in claim 5 wherein said sliding engagement is both in an axial and rotational direction of said bone screw within said internal bore.

7. A method for rigidly connecting a bone screw to an acetabular cup shell, the system comprising:

placing a part-spherical acetabular cup shell having an internal and external surface for contacting the natural acetabulum and at least one aperture therein with a non-circular profile in a prepared acetabulum, said aperture having a cross-section formed by a part-spherical radially inwardly facing surface extending from the internal surface of the shell to the external surface of the shell, said shell aperture including a split-ring mounted therein having a non-circular outer surface and a cylindrical internal bore and including a slot in a wall of said split-ring extending between said internal bore and said outer surface thereof;

inserting a bone screw having a completely cylindrical head portion into the internal bore of the split-ring; and moving said wall of said split-ring with respect to said slot therein by the rotation of the split-ring in the aperture to engage the non-circular ring outer surface with the non-circular profile of the aperture to lock the cylindrical head portion of the bone screw with respect to the radially inwardly facing surface of the aperture in the acetabular cup shell.

8. The method as set forth in claim 7, wherein the split-ring is mounted in the aperture of the shell prior to insertion of the screw.

9. The method as set forth in claim 7, wherein said split-ring is movably mounted in the aperture of the shell.

* * * * *

UNITED STATES PATENT AND TRADEMARK OFFICE
CERTIFICATE OF CORRECTION

PATENT NO. : 7,316,715 B2
APPLICATION NO. : 11/062013
DATED : January 8, 2008
INVENTOR(S) : Gregory E. Plaskon It is certified that error appears in the above-identified patent and that said Letters Patent is hereby corrected as shown below:

Title Page, Item (74) Attorney, Agent, or Firm, "Krumrolz" should read --Krumholz--.
Column 7, line 65, "exerted, by screw" should read --exerted by screw--.
Column 8, line 49, "ivention" should read --invention--.

Signed and Sealed this

Twenty-seventh Day of January, 2009

JOHN DOLL
*Acting Director of the United States Patent and Trademark Office*